(12) United States Patent
Zirngibl et al.

(10) Patent No.: US 6,814,735 B1
(45) Date of Patent: Nov. 9, 2004

(54) DEVICE FOR ALIGNING A GUIDE TEMPLATE

(75) Inventors: Nicolas Zirngibl, Oberwil (CH); Roland Herzog, Waldenburg (CH); Peter Bauer, Basel (CH)

(73) Assignee: Biomet Merck GmbH, Ried b. Kerzers (CH)

( * ) Notice: Subject to any disclaimer, the term of this patent is extended or adjusted under 35 U.S.C. 154(b) by 0 days.

(21) Appl. No.: 10/343,207

(22) PCT Filed: Jul. 28, 2000

(86) PCT No.: PCT/CH00/00410
§ 371 (c)(1),
(2), (4) Date: Jul. 15, 2003

(87) PCT Pub. No.: WO02/09596
PCT Pub. Date: Feb. 7, 2002

(51) Int. Cl.[7] ............................................... A61B 17/58
(52) U.S. Cl. .................................... 606/89; 606/87
(58) Field of Search ........................ 606/86, 104, 96, 606/88, 89, 87

(56) References Cited

U.S. PATENT DOCUMENTS

| | | | | |
|---|---|---|---|---|
| 4,487,203 A | * | 12/1984 | Androphy | 606/88 |
| 5,108,396 A | * | 4/1992 | Lackey et al. | 606/62 |
| 5,122,144 A | | 6/1992 | Bert et al. | |
| 5,254,119 A | * | 10/1993 | Schreiber | 606/87 |
| 5,484,446 A | * | 1/1996 | Burke et al. | 606/87 |
| 5,514,143 A | | 5/1996 | Bonutti et al. | |
| 5,690,637 A | * | 11/1997 | Wen et al. | 606/88 |
| 5,696,668 A | * | 12/1997 | Zenitani et al. | 361/802 |
| 5,911,724 A | * | 6/1999 | Wehrli | 606/88 |
| 5,916,219 A | * | 6/1999 | Matsuno et al. | 606/88 |
| 6,290,704 B1 | * | 9/2001 | Burkinshaw et al. | 606/88 |
| 6,685,711 B2 | * | 2/2004 | Axelson et al. | 606/88 |
| 6,712,824 B2 | * | 3/2004 | Millard et al. | 606/87 |

FOREIGN PATENT DOCUMENTS

| | | |
|---|---|---|
| EP | 0 378 294 A1 | 7/1990 |
| FR | 2 664 157 A1 | 1/1992 |

* cited by examiner

*Primary Examiner*—Pedro Philogene
*Assistant Examiner*—David A Bonderer
(74) *Attorney, Agent, or Firm*—Rankin, Hill, Porter & Clark LLP

(57) ABSTRACT

A device for aligning a guide template used in resecting a distal femur in a one-compartment joint replacement. The device includes first and second support members (12;5), at least one rod-like transverse coupler (10;12), and a guide template (20). The support members each include a support surface (3;6) that is adjustable to lie in one plane (1) and designed to bear against one condyle (24;25) of a femur (21). The transverse coupler is arranged parallel to a transverse axis (2), which, in its end portion, is connected to the first support member (12) and is releasably connectable to the second support member (5). The transverse axis (2) extends parallel to a plane (1). The guide template (20) is displaceable parallel to the plane (1) relative to the second support member (5) and releasably lockable thereon. The second support member (5) is secured against rotation about the transverse axis (2) while being displaceable coaxially with the transverse axis (2) on the at least one transverse coupler (10;12), and is releasably lockable on the transverse coupler.

9 Claims, 3 Drawing Sheets

DEVICE FOR ALIGNING A GUIDE TEMPLATE

BACKGROUND OF THE INVENTION

1. Field of the Invention

The invention relates to a device for the alignment of a guide template permitting to perform a resection of the distal femur in one-compartment joint replacements.

2. Description of Related Art

In surgical operations, a mechanical tool guidance by means of cutting guide heads or drill templates and saw guide slots is often indispensable for the realization of an exact osteotomy or resection of bone, as necessary, for example, for the implantation of a joint endoprosthesis.

A device including a plurality of precision instruments for realizing saw cuts in bone, particularly in the distal part of the femur adjoining the knee-joint and in the tibia, is known from U.S. Pat. No. 4,524,766 to Petersen. The different resection cuts to be made on the femur and on the tibia are realized with this known device by means of different precision instruments that are sequentially attached to the femur or to the tibia. These known precision instruments serve for aligning the templates, which are subsequently screwed onto the bone. After that, the precision instruments may be removed and the cuts may be performed by the surgeon.

Another device of this type is known from EP 322363 to Wehrli. With this known device, the guide templates are equally aligned using a previously affixed equipment of instruments and are then screwed onto the bone. The disclosed equipment of instruments includes two attachment arms laterally fixed on the tibia by means of two Schanz screws, and a measuring rod preferably fastened to the attachment arms at a distance of about 10 cm from the tibial axis. The measuring rod is provided with a guide rail on which the template is displaceably mounted so as to be capable of being moved with great precision into the desired position.

The known devices mentioned above both suffer from the disadvantage of having a relatively big volume, which necessitates big openings to be made in the soft tissues surrounding the joint.

SUMMARY OF THE INVENTION

The invention is intended to provide a remedy for this. It is accordingly an object of the invention to provide a device for aligning guide templates, said device having a minimum volume.

The object to be achieved by the invention is to make it possible, by its application, to restore the natural geometry of the knee. Particularly in connection with a one-condyle (one-compartment) knee replacement (sliding prosthesis) it is of great importance to optimally adapt the prosthesis to the natural circumstances. In doing so, particular attention must be paid to the line of the knee-joint and to the ligamentous apparatus.

According to the invention, this object is achieved by means of a device for aligning a guide template permitting resection of the distal femur in connection with one-compartment joint replacements.

The device according to the invention comprises essentially two support members each having one support surface that can be arranged so as to lie in one plane and are designed to bear each against one condyle of a femur, at least one rod-like transverse coupler arranged parallel to the transverse axis, which, in its end portion, is connected to the first support member and which is connectable to the second support member, the transverse axis extending parallel to the plane. The device according to the invention further comprises a guide template. The guide template is displaceable parallel to the plane and relative to the second support member by means of positioning means and is releasably lockable thereon in any desired position. In addition, the second support member is arranged so as to be secured against rotation relative to the transverse axis and displaceable coaxially to the transverse axis on the at least one transverse coupler and equally lockable in any desired position, so that the support surfaces may be adapted individually to the varying distances between the medial and lateral condyles of different femora.

In the preferred embodiment of the device according to the invention, the second support member comprises an insert including the second support surface. The insert is displaceable coaxially to a central axis extending perpendicularly to the plane and relative to the second support member. Due to this configuration, the insert, which includes the second support surface, may be displaced parallel to the plane, which permits an individual adaptation of the insert carrying the second support surface as may be necessary, for example in the case of a heavily worn medial or lateral condyle.

Preferably, the second support member includes a bore extending parallel to the central axis and provided with an internal screw thread, so that the insert is displaceable coaxially to the central axis by means of a set screw, which may be screwed into the internal screw thread.

In another embodiment of the device according to the invention, the device comprises a first transverse coupler and a second transverse coupler. The second support member is provided with two parallel bores for receiving the transverse couplers, so that the second support member is displaceable on the transverse couplers so as to be secured against rotation about the transverse axis and is lockable by means of a first locating screw.

In yet another embodiment of the device according to the invention, the positioning means comprise at least one rod segment of the transverse coupler projecting over the second support member on the side opposite to the first support member, and a second locating screw, so that the guide template is displaceable coaxially to the transverse axis so as to be secured against rotation about the transverse axis and is releasably lockable by means of the second locating screw. In this embodiment, the guide template is moved close to the femur from a medial or lateral position.

In another embodiment of the device according to the invention, the positioning means comprise at least one longitudinal carrier arranged parallel to a longitudinal axis and connected to a second support member, as well as a second locating screw. The longitudinal axis extends parallel to the plane and perpendicularly to the transverse axis. By displacing the guide template on the at least one longitudinal carrier, it is possible to move the template close to the femur from a ventral position.

The advantages achieved by the present invention consist essentially in the fact that due to its small volume the device according to the invention makes it possible to keep small the incisions that have to be made in the soft tissues surrounding the joint. By making it possible to use a minimally invasive surgical technique, only a small skin incision is required, which means that patients will lose smaller amounts of blood and they will recover more rapidly while feeling less pain.

In addition, there is no need for an intramedullary opening of the femur, and thus no risk of thrombosis formation nor of a wound that might start bleeding again.

A further advantage resides in the fact that fewer surgical instruments are needed, which simplifies the surgical technique and permits the operating room staff to work with a more light-weight case of instruments. In addition, fewer operation steps are necessary, which reduces the time spent on the individual surgical interventions.

BRIEF DESCRIPTION OF THE DRAWINGS

In the following, the invention and improvements of the invention will be illustrated in greater detail with reference to the partially diagrammatic representations of several embodiments, wherein.

DETAILED DESCRIPTION OF THE PREFERRED EMBODIMENTS

Figure 1:
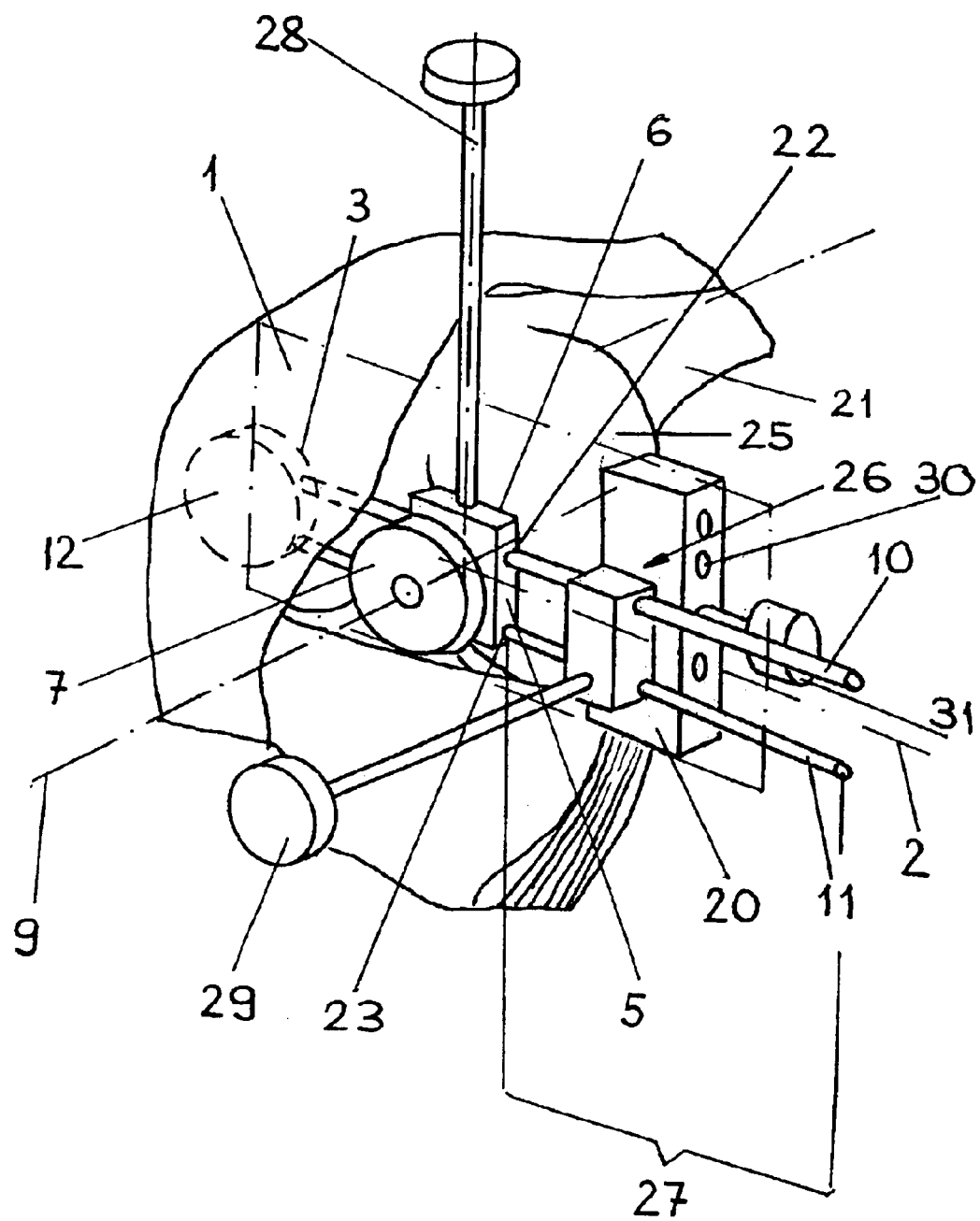
FIG. 1 is a perspective view of one embodiment of the device according to the invention.

FIG. 1 shows an embodiment of the device according to the invention in which the guide template 20 for the distal femoral cut in one-compartment joint replacements is moved close to the femur 21 from a medial or lateral position. The device comprises two support members 5;12 provided with one support surface 3;6, respectively, which are made to bear against the condyles of the distal femur, two rod-like transverse couplers 10;11 arranged parallel to the transverse axis 2 and equally parallel to the plane 1, and a guide template 20. The first support member 12 is moved under the knee-cap, which has been pushed aside, and is applied distally on the intact condyle. In order to avoid injury of the cartilage of the condyle, the first support member 12 is made of plastic material. The second support member 5 comprises an insert 13 including a second support surface 6 (FIG. 3) that is movable by means of a set screw 7 coaxially to a plane 1 extending perpendicularly to the central axis 9 so as to be displaceable relative to the second support member 5. The displacement of the second support surface 6 coaxially to the central axis 9 serves for compensating cartilage attrition on the injured condyle 25, which makes it possible to adjust the joint line of the knee joint after the operation. If the set screw 7 is screwed back to such an extent that the insert 13 (FIG. 3) abuts on the second support member 5, a portion of bone corresponding exactly to the thickness of the artificial knee joint replacement will be resected, as would be required in fact in the case of an almost intact condyle. The more the set screw 7 is screwed forward, the smaller will be the amount of bone resected. In cases of heavily damaged condyles, the set screw may be screwed forward to a maximum of 3 mm. The second support member 5 is made of metal and has a through bore extending coaxially to the central axis 9.

The transverse couplers 10;11 in one end portion are fixedly attached to the first support member 12, whereas the second support member 5 is provided with two bores 22;23 extending parallel to the transverse axis 2 and designed to receive that transverse couplers 10;11, so that the second support member 5 is displaceable on the transverse couplers 10;11 in such a way as to be secured against rotation about the transverse axis 2. Thus it is possible to modify the axial distance of the two support surfaces 3;6 relative to the transverse axis 2, in accordance with the dimension of the knee. This adaptation is to be done in such a way that the support surfaces 3;6 rest on the highest points of the condyles. By means of the first locating screw 28, provided on the second support member 5 and extending parallel to the plane 1 and perpendicularly to the transverse axis 2, the second support member 5 may be releasably locked on the transverse couplers 10;11 at the desired distance from the support member 12. The first locating screw 28 further serves for aligning the device relative to the mechanical axis of the femur 21 and has therefore a relatively great length. Once the device has been aligned relative to the mechanical axis of the femur 21, the device is affixed to the injured condyle 25 by means of a pin (not shown) penetrating through the perforated set screw 7.

By means of positioning means 26, which comprise two rod segments 27 of the transverse couplers 10;11 arranged on the side opposite to the first support member 12 and projecting over the second support member 5, and a second locating screw 29, the guide template 20 realized in the form of a cutting block may be displaced coaxially to the transverse axis 2 in such a way that it is secured against rotation about the transverse axis 2 and may be releasably locked by means of the second locating screw 29. The second locating screw 29 is equally of great length and also serves for aligning the device, as does the first locating screw 28. The guide template 20 is displaced on the transverse couplers 10;11 until it abuts on the injured condyle. After that, the second locating screw 29 is tightened and the guide template 20 is thus fixed on the transverse couplers 10;11.

In addition, the guide template 20 is provided with attachment bores 30 (FIG. 2) extending parallel to the plane 1 and parallel to the transverse axis 2. Once the device has been aligned on the femur 21 and the guide template 20 has been fixed on the transverse couplers 10;11, the guide template 20 is affixed to the femur 21 by means of pins (not shown) inserted through the attachment bores 30. After the insertion of the pins, the connection screw 31 (FIG. 2) connecting the guide template 20 with the positioning means 26 is released, the pin is withdrawn from the set screw 7 and the alignment instruments are removed. Thus, the resection of the femur 21 is realized with only the guide template 20 remaining on the femur 21.

Figure 2:
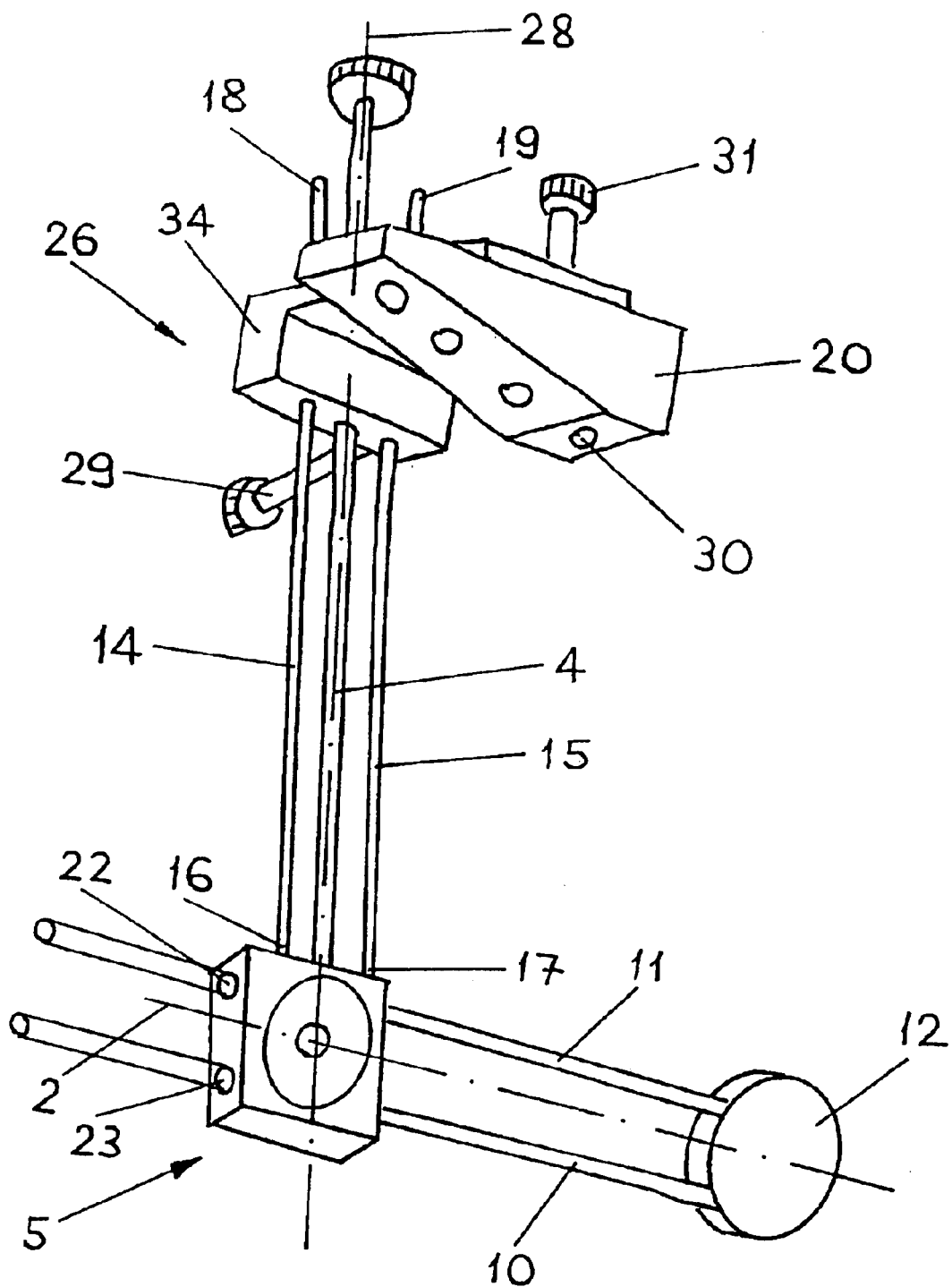
FIG. 2 is a perspective view of another embodiment of the device according to the invention.

FIG. 2 shows an embodiment of the device according to the invention which differs from the embodiment shown in FIG. 1 only insofar as the positioning means 23 comprise two longitudinal carriers 14;15. The two longitudinal carriers 14;15 have first end portions 16;17, second end portions 18;19, and are arranged parallel to a longitudinal axis 4, which extends parallel to the plane 1 (FIG. 1 ) and perpendicularly to the transverse axis 2. The longitudinal carriers 14;15 are connected with their first end portions 16;17 to the second support member 5 and ventrally project therefrom. By means of a connecting member 34, the guide template 20 is connected to the longitudinal carriers 14;15 in such a way as to be secured against rotation about the longitudinal axis 4 while remaining displaceable coaxially to the longitudinal axis 4. By analogy with the embodiment shown in FIG. 1, the device comprises a second locating screw 29 by means of which the connecting member 34 is axially lockable in a desired position on the longitudinal carriers 14;15. The connection between the guide template 20 and the connecting member 34 is assured by means of a connection screw 31. The guide template 20 is provided with attachment bores 30 extending parallel to the plane 1 and parallel to the longitudinal axis 4, so that the guide template 20 may be affixed to the femur 21 by means of pins (not shown) which are inserted through the attachment bores 30. The second support member 5 has a superior bore 22 and an inferior bore 23 extending parallel to the transverse axis 2 and designed to receive the two transverse couplers 10;11 so that the second support member 5 is displaceable on the transverse couplers 10;11 in such a way as to be secured against rotation about the transverse axis 2 and may be locked thereon by means of the first locating screw 28.

Figure 3:
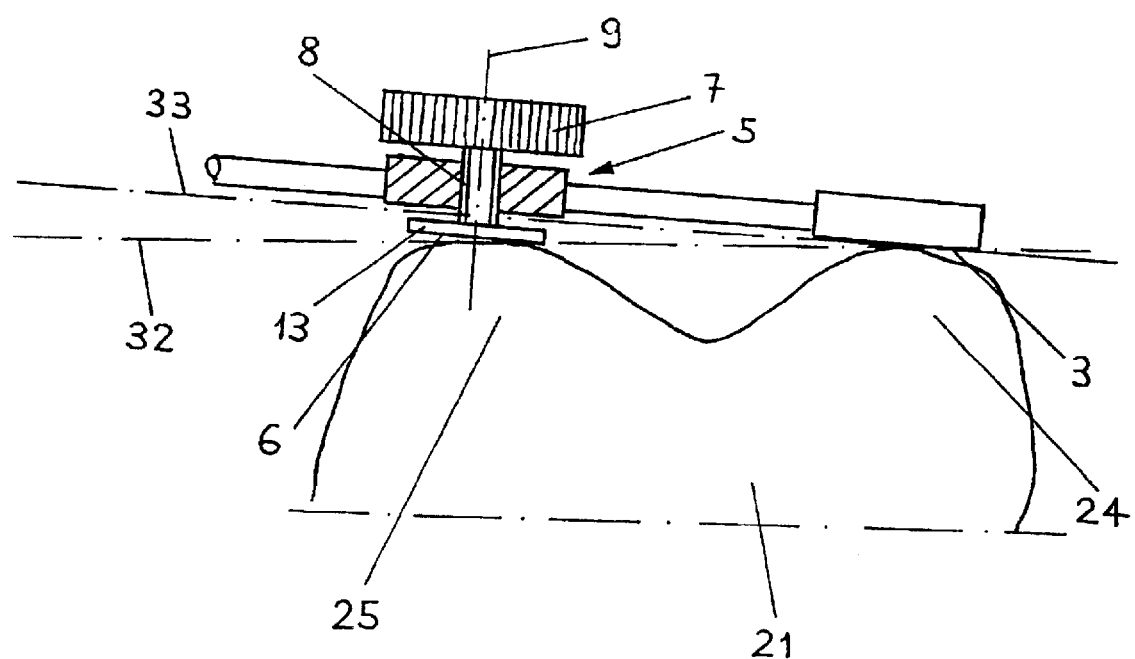
FIG. 3 is a view from an anterior position of the femur including first and second support members bearing thereon according to one embodiment of the inventive device.

FIG. 3 shows a sectional view of the second support member 5. In this embodiment of the device according to the invention, the second support member 5 comprises a bore extending coaxially to the central axis 9 and provided with an internal screw thread 8, so that the insert 13 is displaceable coaxially to the central axis 9 by means of a set screw 7 which may be screwed into the internal screw thread 8. The support surfaces 3;6 rest on the highest points of the distal condyles 24;25. The set screw 7 is screwed out so that the second support surface 6 rests on the injured condyle 25. Thus, the two support surfaces 3;6 serve to adjust a line 32 of the knee joint that produces the "old" knee joint line 32 corresponding to the injured condition of the knee joint. The "new" knee joint line 33 represents the knee joint line 33 after the implantation of the knee joint replacement.

What is claimed is:

1. A device for aligning a surgical instrument in connection with one compartment knee-joint replacements, comprising:

A) first and second support members (12;5), said first support member having a first support surface (3) and said second support member having a second support surface (6), each of said support surfaces (3;6) being adapted to bear against one condyle (24;25) of a femur (21);

B) at least one rod-like transverse coupler (10;11) arranged parallel to a transverse axis (2) that intersects both condyles (24;25), said at least one rod-like transverse coupler having an end portion that is connected to the first support member (12) and releasably connectable to the second support member (5), wherein the transverse axis (2) extends parallel to a plane (1); and C) at least one guide template (20), the guide template (20) being displaceable parallel to the plane (1) relative to the second support member (5) and releasably lockable thereon via a positioning means (26); and wherein D) the second support member (5) is secured against rotation about the transverse axis (2) while being displaceable coaxially with the transverse axis (2) on the at least one transverse coupler (10;12) and releasably lockable thereon.

2. The device as claimed in claim 1, wherein the second support member (5) comprises an insert (13) that includes the second support surface (6), said insert (13) being displaceable relative to the second support member (5) and coaxially with a central axis (9) extending perpendicularly to the plane (1).

3. The device as claimed in claim 2, wherein the second support member (5) comprises a bore extending coaxially with the central axis (9) and provided with an internal screw thread (8), and wherein the insert (13) is displaceable coaxially with the central axis (9) by a set screw (7), which may be screwed into the internal screw thread (8).

4. The device as claimed in claim 1, wherein said at least one transverse coupler comprises a first transverse coupler (10) and a second transverse coupler (11), and wherein the second support member (5) is provided with two parallel bores (22;23) for receiving the transverse couplers (10;11) so that the second support member (5) is displaceable on the transverse couplers (10;11) while being secured against rotation about the transverse axis (2).

5. The device as claimed in claim 1, wherein the positioning means (26) comprises a locating screw (29) and at least one rod segment (27) of the transverse couplers (10;11) projecting over the second support member (5) on a side opposite to the first support member (12), the guide template (20) being secured against rotation about the transverse axes (2;28), displaceable coaxially to the transverse axis (2), and releasably lockable by the locating screw (29).

6. The device as claimed in claim 1, wherein the positioning means (26) comprises at least one longitudinal carrier (14;15) arranged parallel to a longitudinal axis (4) and a locating screw (29), the at least one longitudinal carrier (14;15) having at least one first end portion (16;17), at least one second end portion (18;19), and being connectable to the second support member (5) on the at least one first end portion (16;17) such that the longitudinal axis (4) extends parallel to the plane (1) and perpendicularly to the transverse axis (2), and wherein the guide template (20) is joined to the at least one longitudinal carrier (14;15) so as to be secured against rotation about the longitudinal axis (4) while being displaceable coaxially to the longitudinal axis (4) and releasably lockable thereon by the locating screw (29).

7. The device as claimed in claim 1, wherein first support member (12) is made of plastic material.

8. The device as claimed in claim 1, wherein the support members (5;12) are adjustable so as to lie in one plane.

9. The device as claimed in claim 1, wherein the second support member (5) is secured against rotation about the transverse axis (2) relative to the guide template (20), is displaceable coaxially with the transverse axis (2) on the at least one transverse coupler (10;12), and is releasably lockable on said transverse coupler.

* * * * *